United States Patent [19]

Narayanan et al.

[11] Patent Number: 5,731,264
[45] Date of Patent: Mar. 24, 1998

[54] STABILIZED LIQUID EMULSIFIABLE CONCENTRATE FOR A SULFONYL OR SULFAMOYLUREA HERBICIDE

[75] Inventors: Kolazi S. Narayanan, Wayne; Robert M. Ianniello, Oak Ridge, both of N.J.

[73] Assignee: ISP Investments Inc., Wilmington, Del.

[21] Appl. No.: 733,285

[22] Filed: Oct. 17, 1996

[51] Int. Cl.$^6$ .............................. A01N 25/02; A01N 25/22
[52] U.S. Cl. .............................. 504/116; 504/118; 504/211
[58] Field of Search ............................ 504/116, 211, 504/212, 213, 214, 215, 216, 217, 118

[56] References Cited

U.S. PATENT DOCUMENTS 4,599,412  7/1986  Sandell ............................ 544/211

*Primary Examiner*—S Mark Clardy
*Attorney, Agent, or Firm*—Walter Katz; Marilyn J. Maue; Joshua J. Ward

[57] ABSTRACT

A stabilized liquid emulsifiable concentrate for an active sulfonyl or sulfamoylurea herbicide is described. The liquid delivery system in the concentrate includes a polar solvent capable of dissolving the active herbicide, and which does not promote proton exchange between the active and solvent, suitably gamma-butyrolactone, propylene glycol, acetonitrile, or propylene carbonate; optionally with a hydrophobic solvent; and a mixture of anionic and non-ionic surfactants.

14 Claims, No Drawings

STABILIZED LIQUID EMULSIFIABLE CONCENTRATE FOR A SULFONYL OR SULFAMOYLUREA HERBICIDE

BACKGROUND OF THE INVENTION

1. Field of the Invention

This invention relates to liquid delivery systems for active agricultural chemicals, and, more particularly, to a stabilized liquid emulsifiable concentrate for a sulfonyl or sulfamoylurea herbicide.

2. Description of the Prior Art

Sulfonyl or sulfamoylurea herbicides are very susceptible to hydrolysis in water or in admixture with other polar solvent which promote proton exchange between the active compound and the solvent. Accordingly, such compounds ordinarily are stored before application in the form of a solid delivery system only. However, it would be advantageous to provide a liquid delivery system for such compounds, preferably to provide a liquid emulsifiable concentrate which would be stable both during storage and when added to water to form a tank mix suitable for application to a plant site.

SUMMARY OF THE INVENTION

A stabilized liquid emulsifiable concentrate for a sulfonyl or sulfamoylurea herbicide is described herein, which is stabilized during storage for an extended period of time and usable upon dilution in water, comprises, by weight, (a) about 0.1–50% of one or more sulfonyl or sulfamoylurea herbicides, optionally, (b) in admixture with about 20–50% of one or more diluent agchemicals, (c) about 5–95% of a polar solvent selected from the group consisting of gamma-butyrolactone, acetonitrile, propylene glycol and propylene carbonate, and mixtures thereof, optionally, (d) about 1–90% of a hydrophobic solvent selected from the group consisting of vegetable oil, castor oil, petroleum distillates, esters of $C_6$–$C_{18}$ alkyl acetates, esters of $C_1$–$C_4$ carboxylic acid and $C_6$–$C_{18}$ alcohols, $C_6$–$C_{18}$ alkyl carbonates, $C_6$–$C_{18}$ diols, sterically hindered $C_6$–$C_{18}$ N-alkyl pyrrolidones and $\alpha$-$C_1$–$C_4$ alkyl derivatives thereof, and limonene, and mixtures thereof, and (e) about 5–35% of a mixture of anionic and nonionic surfactants, and, optionally, (f) a buffering agent to provide a pH of about 4–8 upon addition of the concentrate to water in a dilution ratio of about 1:10.

DETAILED DESCRIPTION OF THE INVENTION

The active agricultural chemical in the present invention is a sulfonyl or sulfamoylurea having the general formula:

$$X-(N)_n-SO_2-\underset{R_3}{\underset{|}{N}}-\underset{O}{\underset{\|}{C}}-\underset{R_2}{\underset{|}{N}}-Y$$
$$\phantom{X-(N)_n-SO_2-N}\phantom{-}R_1$$

where

X is a substituted aromatic/heterocyclic moiety or an electron withdrawing group e.g. a substituted sulfonamyl group;

Y is a heterocyclic moiety;

$R_1/R_2/R_3$ is hydrogen or a lower alkyl group.

Accordingly, when n=0 the formula is a sulfonylurea, e.g. Metsulfuron® methyl (duPont); and when n=1 the formula is a sulfamoylurea, e.g. Cyclosulfamuron® (American Cyanamid).

Both the sulfonyl and sulfamoylurea compounds have a labile sulfonamide bridge which is susceptible to hydrolysis in the presence of water or in admixture with another polar solvent. In this system, proton exchange is promoted between the solvent and the compound followed by reaction with water.

Typical active agricultural compounds solubilized herein are shown below:

| X | Y | NAME | |
|---|---|---|---|
| 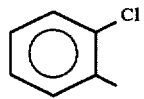 | 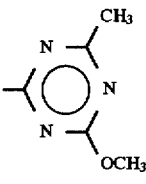 | Chlorsulfuron | DuPont |
| 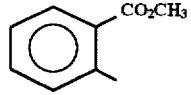 | 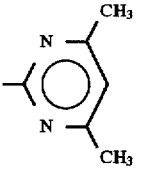 | Sulfometuron methyl | DuPont |
| 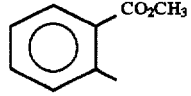 | 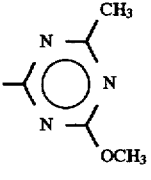 | Metsulfuron methyl | DuPont |

-continued

| X | Y | NAME | |
|---|---|---|---|
| 2-(ethoxycarbonyl)phenyl (CO₂C₂H₅ on benzene) | 4-chloro-6-methoxypyrimidin-2-yl | Chlorimuron ethyl | DuPont |
| 2-(methoxycarbonylmethyl)phenyl (o-CH₂-C₆H₄-CO₂CH₃) | 4,6-dimethyl...4-methyl-6-methoxypyrimidin-2-yl | Bensulfuron methyl | DuPont |
| 3-methyl-2-(methoxycarbonyl)thiophene | 4-methyl-6-methoxy-1,3,5-triazin-2-yl | Thifensulfuron methyl | DuPont |
| methyl 3-chloro-1-methyl-5-(methyl)pyrazole-4-carboxylate | 4,6-dimethoxypyrimidin-2-yl | Halosulfuron methyl | Nissan/Monsanto |
| 2-(3,3,3-trifluoropropyl)phenyl (CH₂CH₂CF₃) | 4-methoxy-6-methyl-1,3,5-triazin-2-yl | Prosulfuron | Ciba Geigy |
| 2-(methoxycarbonyl)phenyl | 4,6-bis(difluoromethoxy)pyrimidin-2-yl (OCHF₂) | Primisulfuron methyl | Ciba Geigy |
| 2-(2-chloroethoxy)phenyl (OCH₂CH₂Cl) | 4-methoxy-6-methyl-1,3,5-triazin-2-yl | Triasulfuron | Ciba Geigy |
| 2-ethoxyphenoxy (OCH₂CH₃, O-) | 4,6-dimethoxypyrimidin-2-yl | Ethoxysulfuron | Agrevo |

-continued
| X | Y | NAME | |
|---|---|---|---|
| 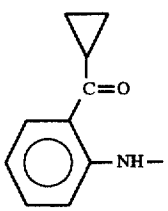 | 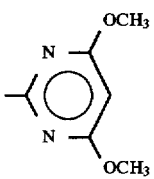 | Cyclosulfamuron | Am Cy |
| 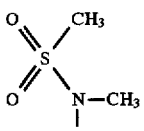 | 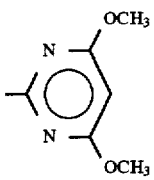 | Amidosulfuron | Agrevo |
| 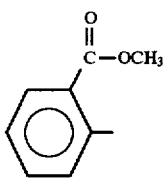 | 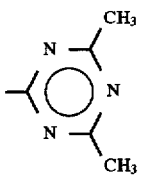 | DPXL 5300 | DuPont |
| 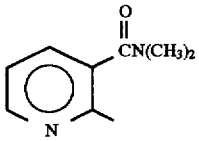 | 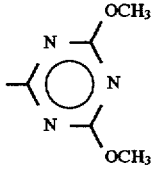 | Nicosulfuron | DuPont |
| 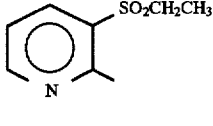 | 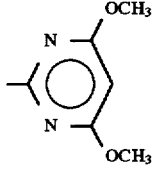 | Rimsulfuron | DuPont |
| 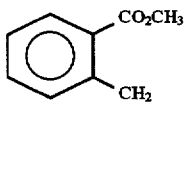 | 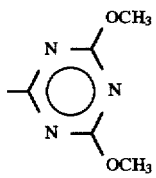 | Londax | DuPont |
| 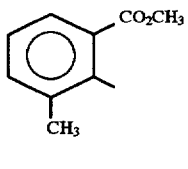 | 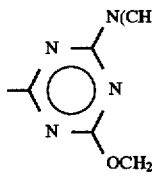 | Triflusulfuronmethyl | DuPont |
| 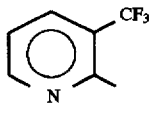 | 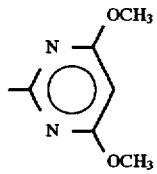 | Flazasulfuron | Ishihara |

-continued

| X | Y | NAME | |
|---|---|------|---|
| (thiophene-C(=O)-OCH₃ structure) | (triazine with OCH₃, N, CH₃ substituents) | Trifensulfuron methyl | DuPont |

Sulfonylurea herbicides are effective at very low doses, i.e. at a rate of application of only grams per acre. However, it is important to avoid an overdose during use. For this reason, sulfonylureas generally are used in combination with a diluent agchemical in an amount of about 20–50% by weight of the concentrate. Such diluent agchemicals usually have broad spectrum activity at a dosage rate of lbs per acre. Another advantage of using diluent agchemicals in the concentrate is that while sulfonylureas are available commercially only as solids, the diluent agchemical can be obtained in liquid form, e.g. as an emulsifiable concentrate. Accordingly, their admixture will provide a diluted liquid premix of the active for transport and use in preparing the stabilized liquid emulsifiable concentrate of the invention.

Some examples of diluent agchemicals for use herein include:

(1) Phenoxy compounds: e.g. phenoxy acetates (MCPA esters), phenoxy propionates, and phenoxy butyrates (MCPB esters);
(2) Benzoates (e.g. Dicamba);
(3) Chloroacetamide/chloroacetanilides (e.g. Alachlor, Acetachlor, and Metolachlor);
(4) Triazine derivatives (e.g. Metrubuzin), Triazinone (e.g. Metamitron);
(5) Carbanilates (e.g. Phenmedipharm);
(6) Thiocarbamates (e.g. Thibencarb); and
(7) Phenylurea (e.g. Linuron and Diuron).

The liquid delivery system in the stabilized liquid emulsifiable concentrate of the invention includes a polar solvent, such as gamma-butyrolactone, propylene glycol or propylene carbonate, or mixtures thereof, preferably gamma-butyrolactone. These polar solvent compounds are capable of dissolving the sulfonylurea without catalyzing proton exchange between the solvent and active, which would result in an undesired hydrolysis in the presence of water. Suitably the polar solvent is present in the concentrate in an amount of about 5–95% by weight of the concentrate. Optionally, about 1–90% by weight of a hydrophobic solvent may be included in the solvent delivery system to enhance the advantageous characteristics of the stabilized concentrate.

The presence in these solvent components, in combination with a mixture of anionic and nonionic surfactants, provides an advantageous liquid delivery system for the agchemicals. Such system provides a suitable emulsifiable concentrate for the active which will form a stable emulsion upon addition to water.

Optionally, a buffering agent may be included therein to provide a pH of about 4–8 upon addition of the concentrate to water in a dilution ratio of about 1:10.

The system of the invention also may be formed from a twin pack comprising, (a) a liquid solution of about 0.1–95% by weight of the active sulfonylurea compound and about 5–99.9% by weight of the polar solvent, and (b) a mixture of anionic and non-ionic surfactants, and optional hydrophobic solvent, diluent agchemical and buffering agent. The twin pack may be admixed before use and then diluted with water to provide the desired liquid delivery system of the invention as a suitable tank mix.

Representative formulations of the invention are shown in Table 1. Related comparative formulations are presented as Comparative Examples D and E. Table 2 shows the stability data for these examples. The standard for a stabilized delivery system is considered a half-life, $t_{1/2}$, at ambient conditions, of at least 2 years. Invention Examples A through C, accordingly, demonstrate a half-life of 2–5 years, (estimated) whereas Comparative Examples D and E have a $t_{1/2}$ of only 8 months to 1 year.

TABLE 1

LIQUID EMULSIFIABLE CONCENTRATE

| | Invention Examples | | | Comparative Examples | |
|---|---|---|---|---|---|
| | % wt. | | | | |
| Components | A | B | C | D | E |
| Agchemicals | | | | | |
| Active | | | | | |
| Metsulfuron ® methyl*- (duPont) a sulfonylurea | 0.34 | 0.34 | 0.34 | 0.34 | 0.34 |
| Diluent | | | | | |
| MCPA Isooctyl ester- (isoctyl-2-methyl-4-chlorophenoxy acetate) | 40 | 40 | 40 | 40 | 40 |
| Polar Solvent | | | | | |
| NMP (N-methylpyrrolidone) | 0 | 0 | 0 | 0 | 8.26 |
| BLO (gamma-butyrolactone) | 9.96 | 9.96 | 35.0 | 25.0 | 0 |
| Hydrophobic Solvent | | | | | |
| NOP (N-octylpyrrolidone) | 0 | 0 | 4.26 | 14.26 | 31.0 |
| EXXATE ® 700 (mixed alkyl acetates) (EXXON) | 0 | 28.9 | 0 | 0 | 0 |
| Castor Oil | 28.9 | 0 | 0 | 0 | 0 |
| Surfactants | | | | | |
| Anionic | | | | | |
| Rhodofac ® RM 710 (Rhone-Poulenc) (Dionylphenol-ethoxylated phosphoric acid) | 4.0 | 4.0 | 2.0 | 2.0 | 2.0 |
| Non-Ionic | | | | | |
| Alkamul EL ® 719 (Rhone - Poulenc) | 16.0 | 16.0 | 18.0 | 18.0 | 18.0 |

TABLE 1-continued

LIQUID EMULSIFIABLE CONCENTRATE

|  | Invention Examples | | | Comparative Examples | |
|---|---|---|---|---|---|
|  | % wt. | | | | |
| Components | A | B | C | D | E |
| Castor Oil 40 EO | | | | | |
| Buffer | | | | | |
| TEA | 0.80 | 0.8 | 0.4 | 0.4 | 0.4 |
| Triethanolamine | | | | | |
| Total | 100.0 | 100.0 | 100.0 | 100.0 | 100.0 |

TABLE 2

Stability Data

| | | | | | |
|---|---|---|---|---|---|
| $t_{1/2}$ (days) at 52° C. | 5.8 | 2.9 | 3.0 | 1.0 | 0.8 |
| $t_{1/2}$ years, at ambient conditions (estimated) | 5 | 2 | 2 | 1 | 0.7* |

*HPLC analysis of sample stored under ambient conditions

TABLE 3

STABILITY OF METSULFURON ® METHYL IN DIFFERENT SOLVENTS AT 52° C.

| | Invention Examples | | | Non-Working Examples | | |
|---|---|---|---|---|---|---|
| Time*, t (days) | BLO | Aceto-nitrile | Propylene Carbonate | N-Methyl-Pyrrolidone | N-Octyl Pyrrolidone | N-Tert-butyl Pyrrolidone |
| 0 | 0.33 | 0.32 | 0.33 | 0.33 | 0.33 | 0.33 |
| 2 | 0.30 | 0.28 | 0.29 | 0.01 | 0.05 | 0.02 |
| 3 | 0.25 | 0.25 | 0.24 | 0.01 | 0.01 | 0.01 |
| 5 | 0.25 | 0.23 | 0.23 | 0.01 | 0.01 | 0.01 |

*Concentration of Active Present After Time t

Table 3 shows the extent of stability of solutions of active with individual polar solvents. Excellent stability was achieved when formulating the active with gamma-butyrolactone, acetonitrile or propylene carbonate, whereas the active decomposed rapidly in pyrrolidone solvents. Accordingly, the active may be stored in suitable polar solvents, e.g. gamma-butyrolactone, before admixture with the other ingredients of the emulsifiable concentrate.

While the invention has been described with particular reference to certain embodiments thereof, it will be understood that changes and modifications may be made which are within the skill of the art. Accordingly, it is intended to be bound only by the following claims, in which:

What is claimed is:

1. A liquid emulsifiable concentrate of an active agricultural chemical which is stabilized during storage for an extended period of time, and usable upon dilution in water, comprising, by weight, (a) about 0.1–50% of one or more free sulfonyl or sulfamoylurea herbicides, which are ordinarily susceptible to hydrolysis in liquid formulations, optionally, (b) in admixture with about 20–50% of one or more diluent agchemicals, (c) about 5–95% of a polar solvent selected from the group consisting of gamma-butyrolactone, propylene glycol, propylene carbonate and acetonitrile, and mixtures thereof, (d) optionally, about 1–90% of a hydrophobic solvent selected from the group consisting of vegetable oil, castor oil, petroleum distillates, esters of $C_6$–$C_{18}$ alkyl acetates, esters of $C_1$–$C_4$ carboxylic acid and $C_6$–$C_{18}$ alcohols, $C_6$–$C_{18}$ alkyl carbonates, $C_6$–$C_{18}$ diols, sterically hindered $C_6$–$C_{18}$ N-alkyl pyrrolidones and $\alpha$-$C_1$–$C_4$ alkyl derivatives thereof, and limonene, and mixtures thereof, (e) about 5–35% of a mixture of anionic and non-ionic surfactants, and, (f) optionally, a buffering agent to provide a pH of about 4–8 upon addition to water in a dilution ratio of about 1:10.

2. A concentrate according to claim 1 wherein said active is a sulfonylurea.

3. A concentrate according to claim 1 wherein said active is a sulfamoylurea.

4. A concentrate according to claim 1 wherein said diluent agchemical is present.

5. A concentrate according to claim 1 wherein the diluent agchemical is a phenoxy acid ester or derivative thereof, a substituted benzoate ester or derivative thereof, a chloroacetamide or chloroacetanilide, a triazine, a carbanilate, a thio carbamate, or a phenylurea.

6. A concentrate according to claim 1 wherein said hydrophobic solvent is present.

7. A concentrate according to claim 1 wherein said buffering agent is present.

8. A concentrate according to claim 1 wherein said polar solvent is gamma-butyrolactone.

9. A stable emulsifiable agricultural liquid delivery solution comprising about 0.1–95% by wt. of a sulfonyl or sulfamoylurea herbicide and about 5–99.9% of a polar solvent selected from the group consisting of gamma-butyrolactone, acetonitrile, propylene carbonate and propylene glycol, and, optionally, 5–35% of a mixture of anionic and non-ionic surfactants.

10. A solution according to claim 9 wherein said solvent is gamma-butyrolactone.

11. A twin pack formulation comprising (a) the solution of claim 8, and (b) a composition comprising a mixture of anionic and non-ionic surfactants, optionally with (1) one or more diluent agchemicals, and/or (2) a hydrophobic solvent, and/or (3) water.

12. A twin pack according to claim 11 wherein a diluent agchemical is present.

13. A twin pack according to claim 12 wherein the hydrophobic solvent is present.

14. A twin pack according to claim 13 wherein water is present.

* * * * *